United States Patent
Kollias et al.

(10) Patent No.: US 6,907,193 B2
(45) Date of Patent: Jun. 14, 2005

(54) METHOD OF TAKING POLARIZED IMAGES OF THE SKIN AND THE USE THEREOF

(75) Inventors: Nikiforos Kollias, Skillman, NJ (US); Kenneth Merola, Agoura Hills, CA (US); Jeffrey S. Pote, Easton, PA (US); Gregory Payonk, Flanders, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 10/007,296

(22) Filed: Nov. 8, 2001

(65) Prior Publication Data

US 2003/0086703 A1 May 8, 2003

(51) Int. Cl.$^7$ .............................................. G03B 15/02
(52) U.S. Cl. .............................. 396/4; 396/14; 396/155; 348/77; 348/371; 600/476; 356/364; 356/369
(58) Field of Search ................................ 396/4, 14, 15, 396/155, 182, 1, 661; 348/77, 370, 371; 600/407, 476; 356/364, 369; 606/9, 10

(56) References Cited

U.S. PATENT DOCUMENTS

| | | |
|---|---|---|
| 3,904,293 A | 9/1975 | Gee |
| 4,170,987 A | 10/1979 | Anselmo et al. |

(Continued)

FOREIGN PATENT DOCUMENTS

| | | | | |
|---|---|---|---|---|
| EP | 0 682 236 | A1 | 11/1995 | |
| EP | 0 737 932 | B1 | 10/1996 | |
| EP | 1 089 208 | A2 | 4/2001 | |
| EP | 1 116 845 | A2 | 7/2001 | |
| EP | 1 194 898 | B1 | 3/2003 | |
| FR | 2 821 152 | A | 8/2002 | |
| GB | 2 106 241 | A | 4/1983 | |
| JP | 07075629 | A * | 3/1995 | ............ A61B/5/00 |
| JP | 07-075829 | | 3/1995 | |
| JP | 7323014 | | 12/1995 | |
| JP | 07323014 | A * | 12/1995 | ............ A61B/5/00 |
| WO | WO 94/24936 | A1 | 11/1994 | |
| WO | WO 98/24360 | A1 | 8/1996 | |
| WO | WO 97/47235 | A1 | 12/1997 | |
| WO | WO 98/37811 | A1 | 9/1998 | |
| WO | WO 00/78398 | A1 | 12/2000 | |
| WO | WO 01/04839 | A2 | 1/2001 | |
| WO | WO 01/35827 | A1 | 5/2001 | |
| WO | WO 01/45557 | A1 | 8/2001 | |
| WO | WO 01/82786 | A2 | 11/2001 | |

OTHER PUBLICATIONS

Anderson, R.R., "Polarized Light Examination and Photography of the Skin", Arch. Dermatol., vol. 127, Jul. 1991 (pp. 1000–1005).*

Anderson R R: Polarized Light Examination and Photography of the Skin Archives of Dermatology, XX, XX, vol. 127, Jul. 1991 (1991–07), pp. 1000–1005, XP000937510 ISSN: 0003–987X.

(Continued)

Primary Examiner—David M. Gray

(57) ABSTRACT

The present invention relates to a method of photographing the skin of a person comprising the steps of: (i) illuminating the skin with at least one light source, where the light emitted from the light source is filtered using a polarizing filter; and (ii) capturing the image of the illuminated skin with a camera; wherein the angle formed by the light source, the skin, and the camera is from about 35 degrees to about 55 degrees.

24 Claims, 1 Drawing Sheet

U.S. PATENT DOCUMENTS

| | | | |
|---|---|---|---|
| 4,395,541 A | | 7/1983 | Jacquet et al. |
| 4,842,523 A | | 6/1989 | Bourdier et al. |
| 4,905,700 A | | 3/1990 | Wokalek et al. |
| 4,911,544 A | | 3/1990 | Walsh |
| 5,005,975 A | | 4/1991 | Kawai et al. |
| 5,016,173 A | * | 5/1991 | Kenet et al. ............... 382/128 |
| 5,198,875 A | * | 3/1993 | Bazin et al. ............... 356/369 |
| 5,241,468 A | | 8/1993 | Kenet |
| 5,363,854 A | * | 11/1994 | Martens et al. ............. 600/477 |
| 5,456,260 A | | 10/1995 | Kollias et al. |
| 5,556,612 A | | 9/1996 | Anderson et al. |
| 5,640,957 A | | 6/1997 | Kaminski et al. |
| 5,742,392 A | | 4/1998 | Anderson et al. |
| 5,836,872 A | * | 11/1998 | Kenet et al. ............... 600/306 |
| 5,991,433 A | | 11/1999 | Osanai et al. |
| 6,018,586 A | | 1/2000 | Kamei |
| 6,032,071 A | * | 2/2000 | Binder ....................... 600/476 |
| 6,081,612 A | | 6/2000 | Gutkowicz-Krusin et al. |
| 6,134,011 A | | 10/2000 | Klein et al. |
| 6,148,092 A | | 11/2000 | Qian |
| 6,208,749 B1 | | 3/2001 | Gutkowicz-Krusin et al. |
| 6,215,893 B1 | | 4/2001 | Leshem et al. |
| 6,251,070 B1 | | 6/2001 | Khazaka |
| 6,293,284 B1 | | 9/2001 | Rigg |
| 6,437,856 B1 | | 8/2002 | Jacques |
| 6,728,560 B2 | | 4/2004 | Kollias et al. |
| 2002/0182235 A1 | | 12/2002 | Slavtcheff et al. |

OTHER PUBLICATIONS

Kollias N. et al.: "Fluoroscence photography in the evaluation of hyperpigmentation in photodamaged skin" Journal of the American Academy of Dermatology, vol. 36, No. 2 Part 1, Feb. 1, 1997 pp. 226–230, XP 008019421.

Muccini J. et al.: "Polarized light photography in the evaluation of photoaging" Journal of the American Academy of Dermatology, vol. 33, No. 5 Part 1—Nov. 1, 1995 pp. 765–769, XP008019420.

U.S. patent application Ser. No. 10/008,753, Johnson & Johnson Consumer Companies, Inc.

U.S. patent application Ser. No. 10/008,579, Johnson & Johnson Consumer Companies, Inc.

U.S. patent application Ser. No. 10/288,907, Johnson & Johnson Consumer Companies, Inc.

Kollias, N., Stamatas, G., Optical Non–Invasive Approaches to Diagnosis of Skin Diseases, Optical Dianosis in Dermatology, 2002, pp. 64–75.

Kligman, A. Fulton, J., Ultraviolet Photography Serves as Both Predictor and Educator, vol. 10, No. 9 Cosmetic Dermatology, 1997, pp. 31–33.

Wilheim, K–P, Elsner, P. Berardesca, E. Maibach, H., Bioengineering of the Skin: Skin Surface Imaging and Analysis, CRC Press, 1997, pp. 331–344.

Hillebrand, G., Miyamoto, K, Schnell, B. Ichihashi, M, Shinkura R, Akiba, S., Quantitative evaluation of skin condition in an epidemiological survey of female living in northern versus southern Japan, Journal of Dermatological Science, 27 Suppl, 1(2001) pp. S42–S52.

Pagnoni, A., Kligman, A., Kollias, N. Goldberg, S., Stoudemayer,T., Digital fluorescence photography can assess the suppersive effect of benzoyl peroxide on Propionibacterium acens, J. Am. Dermatol, vol. 41, No. 5, Part 1, pp. 710–716.

Lucchina, L, Kollias, N. Gillies, R. Phillips, S, Muccini, J. Stiller, M. Trancik, R, Drake, L., Fluorescence photography in the evaluation of acne, Journal of the American Academy of Dermatology vol. 35, No. 1, pp. 58–63.

Phillips, S. Kollias, N. Gillies, R., Muccini, J. Drake, L, Polarized light photography enhances visualization of inflammatory lessions of acne vulgaris, Journal of American Academy of Dermatology, vol. 37, No. 6, pp. 948–952.

* cited by examiner

METHOD OF TAKING POLARIZED IMAGES OF THE SKIN AND THE USE THEREOF

FIELD OF THE INVENTION

The present invention relates to a method of taking polarized images of the skin and the use of such images.

BACKGROUND OF THE INVENTION

In order to promote skin care products, many cosmetic companies ask their potential customers questions regarding perception of their skin. Based on the answers to these questions, cosmetic companies are able to better suggest cosmetic and therapeutic products to these people. Examples of such promotions can be found on the Internet webpages of Neutrogena®, L'Oreal®, and Lancome®. These questions, however, are only based upon the subject's perception of their skin under visible light. Many skin problems, however, are not always visible under such conditions.

Various types of photography have been developed to enhance the visualization of the skin. In visible light photography, or standard photography, the most common arrangement includes a camera and one or more flash units to deliver visible light to the skin by direct illumination, diffuse illumination, or a combination thereof. Angled lighting has also been used to generate a gradient of the illuminating field on the skin in order to enhance the visualization of wrinkles and fine lines. Depending on the direction of the gradient (vertical or horizontal), different sets of wrinkles and fine lines may be visually enhanced.

Polarized light photography has also been developed to selectively enhance either surface or subsurface features of the skin. These results are accomplished by placing a polarizing filter (typically a linear polarizing filter) both in front of the flash unit, and in front of the camera. When the polarizing filters are in the same orientation with each other, surface features of the skin such as scales, wrinkles, fine lines, pores, and hairs are visually enhanced. When the polarizing filters are aligned perpendicular to each other, subsurface features of the skin such as erythema, pigmentation, blood vessels, and hair, are visually enhanced.

Ultraviolet photography, where the flash unit is filtered to produce ultraviolet A light and the camera is filtered so that only visible light enters the lens, has been used to visually enhance the appearance of pigmentation, the bacteria *p. acnes*, and horns. A variation of ultraviolet photography has been termed the "sun camera" where ultraviolet A light is used to illuminate the skin and an ultraviolet A sensitive film or a digital camera is used to record the reflected ultraviolet light from the skin. In this arrangement, both the pigment distribution and the surface features of the skin are visually enhanced.

The present invention provides people with access to one or more of these improved means of viewing their skin, in order to provide them additional insight into the condition of their skin. Such insight allows them to make more informed decisions regarding the purchase of skin care products. In addition, skin care products can be suggested to such potential customers by retailers or professionals based upon such customer's enhanced perception of their skin.

SUMMARY OF THE INVENTION

In one aspect, the invention features a method of promoting a skin care product comprising taking a standard photograph of the skin of a person; (ii) taking at least one additional photograph of the skin of the person, the additional photograph selected from the group consisting of an ultraviolet photograph, a blue fluorescence photograph, and a polarized photograph; (iii) presenting the standard photograph and the at least one additional photograph to the person; and (iv) suggesting skin care products based upon the person's review of the presented photographs.

In another aspect, the invention features a method of photographing the skin of a person comprising the steps of: (i) illuminating the skin with at least one light source, where the light emitted from the light source is filtered using a polarizing filter; and (ii) capturing the image of such illuminated skin with a camera; wherein the angle formed by the light source, the skin, and the camera is from about 35 degrees to about 55 degrees.

In another aspect, the invention features a method of promoting a skin care product comprising: (i) illuminating the skin with at least one light source, where the light emitted from the light source is filtered using a polarizing filter; (ii) capturing the image of such illuminated skin with a camera, wherein the angle formed by the light source, the skin, and the camera is from about 35 degrees to about 55 degrees; (iii) presenting the image to the person; and (iv) suggesting skin care products based upon the person's review of the image.

In another aspect, the invention features a method of photographing the skin of a person comprising: (i) illuminating the skin with at least one light source, wherein the light source either emits substantially only light having a wavelength from about 380 to about 430 nm or emits light through a filter that emits substantially only light having a wavelength from about 380 to about 430 nm; and (ii) capturing the image of such illuminated skin with a camera; wherein the light entering the camera is also filtered with a long pass filter, wherein the long pass filter substantially eliminates light having a wavelength below about 400 nm.

In one aspect, the invention features a method of promoting a skin care product comprising: (i) illuminating the skin with at least one light source, wherein the light source either emits substantially only light having a wavelength from about 380 to about 430 nm or emits light through a filter that emits substantially only light having a wavelength from about 380 to about 430 nm; (ii) capturing the image of such illuminated skin with a camera, wherein the light entering the camera is also filtered with a long pass filter, wherein the long pass filter substantially eliminates light having a wavelength below about 400 nm; (iii) presenting the image to the person; and (iv) suggesting skin care products based upon the person's review of the image.

Other aspects, features, and advantages of the present invention will be apparent from the detailed description of the invention and from the claims

DETAILED DESCRIPTION OF THE INVENTION

Figure 1:
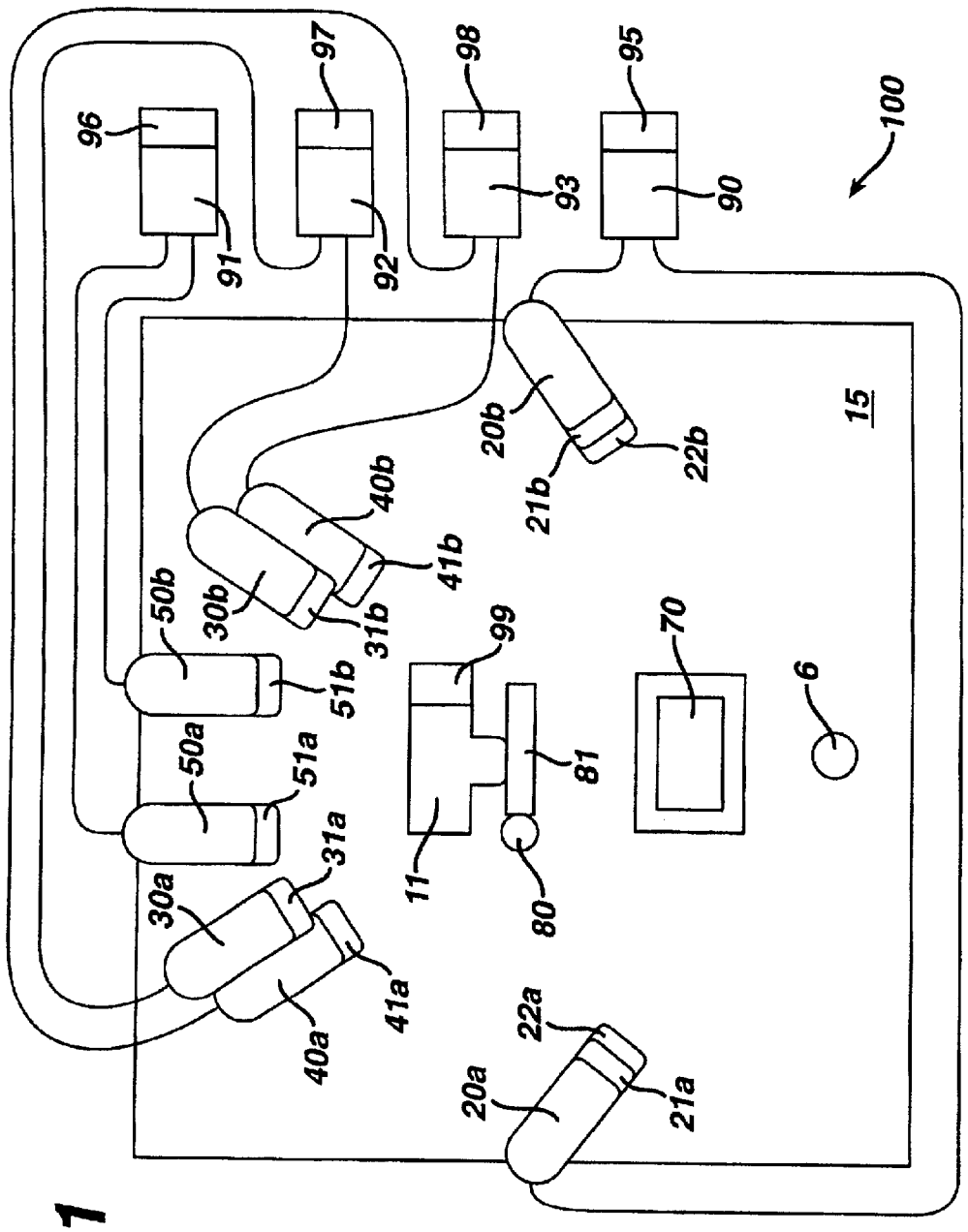
FIG. 1 is an overhead view of an apparatus used to sequentially take the following four types of pictures of a person: a standard photograph, a polarized photograph, a ultraviolet A photograph, and a blue fluorescence photograph.

It is believed that one skilled in the art can, based upon the description herein, utilize the present invention to its fullest extent. The following specific embodiments are to be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

The Camera

Various types of cameras may be used in the methods of the present invention. Examples of such cameras include, but are not limited to, standard 35 mm cameras, cameras using instant developing film (such as those available from Polaroid Corporation, Cambridge, Mass. USA), and digital cameras. Preferably, a digital camera is used as it provides fast access to the images taken of the subject. It also allows the image to be displayed on a large monitor, enables the subject to easily enlarge areas of skin that are of particular interest (e.g., areas of the face), and allows the image to be printed in a report which can also include suggestions for products addressing any concerns the subject noticed upon examining the images. Examples of suitable digital cameras include, but are not limited to, those which take images of at least 1 million pixels, preferable at least 4 million pixels. Examples of such digital cameras include, but are not limited to, the Nikon D1X (Nikon, Tokyo, Japan) and the Fuji S1 (Fuji, Tokyo, Japan).

One or more cameras may also be used in the methods of the present invention, e.g., separate cameras having a distinct light filtering lens may be used for each type of photograph taken and/or separate cameras used to photograph different areas or angles of the subject. Preferably, only one camera is used since having more than one camera would require that the cameras be calibrated to have the same color and intensity response. When only one camera is used, a mechanical filter wheel or arm containing a filter(s) may be placed in front of the camera to selectively filter the light prior to or after entering the camera's lens and/or the respective filter(s) may be placed at the light source(s) to filter the light as it leaves the light source(s). In the case where multiple light sources are used, the camera can communicate with each of the respective light sources via hard wiring or a radio transceiver.

In one embodiment, the camera(s) are mounted at the same level as the area of skin that the subject desires to be photographed, e.g., the face of the subject. Preferably, the camera is set such that such area of skin substantially fills the frame area of the photograph, e.g., to ensure the greatest amount of detail in the image.

In one embodiment where multiple images are acquired by single camera, the images are preferably acquired in less than about 30 seconds, e.g., less than about 10 seconds.

Standard Photography

In one embodiment, the method includes the step of taking a standard photograph of the subject. What is meant by "standard photograph" a photograph that is taken of the subject using visible light (e.g., light having a wavelength from about 400 to about 700 nm). In one embodiment, the subject is illuminated with one or more, preferably two, flash units that emit visible light. In one embodiment, the flash unit(s) are further equipped with a diffusing filter that is placed in front of each flash unit. A diffusing filter is a filter, which assists in uniformly dispersing light (e.g., to help eliminate "hot spots"). Examples of such diffusing filters include, but are not limited to, frosted glass filters such as a Broncolor Diffuser (Sinar Bron, Allschwil, Switzerland), metal grids which may be printed on glass substrates, or a diffusing reflective umbrella for indirect lighting.

In one embodiment, the flash unit(s) are angled at the subject's skin to generate a gradient across the surface of the skin. In a further embodiment, the flash units are mounted higher than the skin area of the subject and aimed at such skin area in order to give a gradient of light on the skin from the top to the bottom. In one embodiment, the angle of the flash units is from about 5 to about 30 degrees, such as about 10 degrees, from horizontal. This gradient visually enhances various features of the skin such as the fine lines and wrinkles in the subject, e.g., the crow's feet around the eye and forehead or mouth area wrinkles.

Polarized Light Photography.

In one embodiment, the method includes the step of taking a polarized photograph of the subject. What is meant by "polarized photograph" is a photograph of the subject taken (i) with a light source that emits light through a polarizing filter and/or (ii) through a polarized filter that filters light prior to or after entering the camera's lens.

In one embodiment, the camera and one or more flash units, preferably two, are on about the same plane as the subject's skin to be photographed, and the flash units are placed so that the angle formed by each flash unit(s), subject's skin, and camera is about 35 to 55 degrees, such as about 45 degrees. In one embodiment, a polarizing filter is placed in front of each flash unit. What is meant by a "polarizing filter" is a filter that filters incoming light to emit substantially only polarized light. What is meant by the term "substantially," as used herein, is at least 75 percent, preferably 90 percent, and most preferably at least 95 percent.

Examples of a polarizing filter include, but are not limited to, polarizing plates such as those available from Edmund Scientific (Barrington, N.J. USA), polarizing prisms such as Glan Thomson polarizing prisms, or a polarizing reflector that reflects light at about the Brewster angle. Polarizing filters may be linear or circular polarizing filters. In a further embodiment, a light diffuser is placed between the flash unit and the polarizing filter.

In one embodiment, a linear polarizing filter is used at the light source and the linear polarizing filter is arranged such that the electric field of the emitted light is about perpendicular to the plane formed by the light source, the person's skin, and the camera. In another embodiment, a linear polarizing filter is used at the light source and the linear polarizing filter is arranged such that the electric field of the emitted light is about parallel to the plane formed by the light source, the person's skin, and the camera.

In a further embodiment, the flash unit(s) are positioned on a horizontal plane with the camera and the subject's skin and the polarizing filter is a linear polarizing filter oriented so that the electric field of the transmitted light is in the vertical direction (e.g., perpendicular to the plane). In this orientation, the critical angle for total internal reflection from within the top corneocytes is 45 degrees, thereby resulting in an image that is dominated by the light thus reflected from the corneocytes. The resulting image has a high degree of glare, which is further enhanced when an optical coupling medium, such as sebum or "oils," is present on the surface of the corneocytes. The polarized image, thereby, allows an estimate to be made as to the oiliness of the subject's skin.

It also provides insight into the number and severity of pores on the cheek and forehead areas of the facial skin. Other desired outcomes of polarized photography include, but are not limited to, an enhanced image of surface features such as fine lines, skin texture, scales and vellous hair.

In another embodiment, the flash unit(s) are positioned on a vertical plane above the camera and the subject's skin so that the angle formed by the flash unit, subject's skin, and camera is about 35 to 55 degrees such as about 45 degrees and flash unit(s) are filtered with linear polarizing filter that is placed with the transmitted electric field in the vertical direction (e.g., parallel to the plane). In this arrangement the surface glare from the skin is minimized, thus, enhancing the subsurface features of the skin, such as erythema (redness), blood vessels, and pigmentation.

Polarized light sources on both on the horizontal and vertical planes with the camera and the subject's skin can be used to enhance specific aspects of the skin (e.g., the face) that are partially shaded with the use of polarized light sources only on the horizontal or vertical planes alone.

In one embodiment, the photograph of the subject is taken both with a light source that emits lights through a polarizing filter and through a polarizing filter that filters the light prior to or after entering the camera's lens. When the polarizing filters are in the same orientation with each other (e.g., both horizontal or both vertical), surface features of the skin such as scales, wrinkles, fine lines, pores, and hairs are visually enhanced.

When the polarizing filters are aligned perpendicular to each other (e.g., one horizontal and one vertical), subsurface features of the skin such as erythema, pigmentation, blood vessels, and hair, are visually enhanced.

Ultraviolet Photography

In one embodiment, the method includes the step of taking an ultraviolet photograph of the subject. What is meant by "ultraviolet photograph" is a photograph of the subject taken (i) with a light source that either emits substantially only ultraviolet light (radiation) or emits light through an ultraviolet filter and/or (ii) through an ultraviolet filter that filters the light prior to or after entering the camera's lens. What is meant by an ultraviolet filter is a filter that filters incoming light to emit substantially only ultraviolet light (e.g., light having a wavelength from about 200 to about 400 nm). Examples of light sources that can emit substantially only ultraviolet light are light emitting diodes. Examples of ultraviolet photography include, but are not limited to, ultraviolet A photography or ultraviolet B photography.

Ultraviolet A Photography.

In one embodiment, the method includes the step of taking an ultraviolet A photograph of the subject. What is meant by "ultraviolet A photograph" is a photograph of the subject taken (i) with a light source that emits substantially only ultraviolet A light or emits light through an ultraviolet A filter and/or (ii) through an ultraviolet A filter that filters the light prior to or after entering the camera's lens.

In one embodiment, one or more, preferably two, flash units are filtered with an ultraviolet A filter ("UVA filter"). What is meant by a UVA filter is a filter that filters incoming light to emit substantially only light having a wavelength of from about 320 to about 400 nm. Examples of UVA filters include, but are not limited to, the ultraviolet UG-11 filter (Schott Glass Technologies, Duryea, Pa. USA). The resulting image may be rich in red color because of the long wavelength pass of UVA filter. In one embodiment, when utilizing a digital camera, either the blue or green channel, preferably the blue channel, of the RGB image is selected for viewing, resulting in a black and white image.

Benefits of an ultraviolet A photograph include, but are not limited to, enhanced appearance of pigmented macules on the skin and surface features such as bumps and wrinkles. Ultraviolet A photography may be used to determine the uniformity of application of topical products, such as sunscreens and of make-ups, that contain materials that absorb ultraviolet radiation. In addition, since melanin pigmentation more strongly absorbs UVA radiation than visible light, illuminating the skin with THEA radiation gives an enhanced contrast between normal skin and hyperpigmented skin. Furthermore, the pigmented macules are visualized as dark spots on a bright background due to the scattering and the fluorescence of the dermal collagen matrix. The image recorded by the camera includes both the reflection of ultraviolet A radiation and fluorescence of the collagen. The resulting black and white image obtained by the blue or green channel from a digital camera provides an enhanced view of the distribution of pigmented macules on the skin (e.g., the face). For subjects with deeply pigmented skin, the red channel may be selected.

In another embodiment, the flash units are further filtered with a red blocking filter. Examples of such red blocking filter include, but is not limited to, a KG-5 filter (Schott Glass Technologies). Such filters may assist in correcting the red appearance of the image.

Blue Fluorescence Photography

In one embodiment, the method includes the step of taking a blue fluorescence photograph of the subject. What is meant by "blue fluorescence photograph" is a photograph of the subject taken with a light source that emits substantially only blue light or emits light through a blue filter. What is meant by "blue light" is light having a wavelength from about 380 to about 430 nm.

In one embodiment, one or more, preferably two, flash units are filtered with a blue filter. What is meant by a "blue filter" is a filter that filters incoming light to emit substantially only blue light. Examples of such blue filters include, but are not limited to, interference filters such as those available from Melles Griot (Irvine, Calif. USA) or dielectric filters.

In one embodiment, the light entering the camera is also filtered (e.g., prior to or after entering the lens of the camera) with a long pass filter to substantially eliminate light having a wavelength below about 400 nm. Examples of long pass filters include, but are not limited to, GG-420 or GG-440 filters (Schott Glass Technologies) and Kodak Wratten No. 8 (Eastman Kodak, Rochester, N.Y. USA). In one embodiment, the flash units and filters are placed on either side of the camera at approximately the same horizontal plane as the skin sample of the subject.

This type of photography produces bright images of the distribution of coproporphyrin produced by the bacteria *P. acnes* and of horns. What is meant by a "horn" is a mixture of sebaceous lipids, keratinocytes, and possibly sebocytes impacted in open comedones and blackheads on the skin. By using substantially only blue light that is within the Soret absorption band of porphyrins, the fluorescence emission of coproporphyrin is maximized. Excitation in this range also yields bright emission images of the distribution of "horns" because the fluorescence yield of horns is higher when excited in the blue region of the spectrum.

In one embodiment, when utilizing a digital camera, the color image may be viewed showing the distribution of coproporphyrin and therefore the sites of maximum *p. acnes* concentration, which appears red in the image. The image also contains bright white spots, which correspond to clogged pores or open comedones. In another embodiment the green channel of the RGB image is selected to enhance the horn fluorescence emission and the red channel may be selected to enhance the fluorescence emission of porphyrins from *p. acnes*. The resulting black and white images, thus, provide excellent imaging of small vessels because hemoglobin has its Soret band in the same wavelength range as porphyrins. In one embodiment, these vessels are visualized using either the blue or the green channel of the RBG image.

Promotion of Skin Care Products

Upon acquisition of the photographs, these images are presented to the subject. The means of presenting the photographs depends in part on the type of photograph taken (e.g., using standard film, instant developing film, or a digital image). When using standard film or instant developing film, the prints of the images are provided to the subject. The prints may also be scanned and presented to the subject on a computer monitor (e.g., a LCD or CRT monitor). When using a digital camera, the image may also be presented on such a monitor.

Following presentation of the images to the subject, skin care products can be suggested to the person based upon his/her review of the images. In one embodiment, the method comprises presenting the subject with one or more questions relating to the presented images. Based upon the answers to such questions, one or more skin care products can be suggested to the subject. These products can be associated with responses to the questionnaire, made by a person reviewing the subject's answers, or made by a computer based upon the answers of the subject. The review of the various images by the subject facilitates more informed answers to the questions.

In one embodiment, the suggestions of skin care products is made by a computer program that recommends products based upon the answers provided by the subject. In one embodiment, a list of skin care products are maintained on a relational database. These products are associated with answers to certain questions. Thus, based upon the answers provided by the subject, certain products are selected by the computer program. For example, if the subject answers that he/she has wrinkles, the computer program will search the data based for skin care products effective for treating wrinkles (e.g., products containing retinol) and/or if the subject answers that he/she has acne, the computer program will search the database for skin care products effective for treating acne (e.g., products containing benzoyl peroxide or salicylic acid).

In one embodiment, these suggestions are limited to a set number of products, e.g., the program will not recommend more than five products. In such a case, the computer program will prioritize skin care product suggestions based upon either the importance of the skin disorders identified by the subject or the database's ranking of importance of the skin disorder to be addressed. For example, if the subject responds that he/she has severe acne and moderate fine lines, the computer program will recommend acne product(s).

In one embodiment, following application of a skin care product (e.g., one suggested by the present method) or a period of time (e.g., one week, one month, or one year), the subject is then photographed again. These new photographs are compared to the original photographs to determine the efficacy of the skin care product.

In one embodiment, the recommended products may be available at the location where the photographs are taken, e.g., the photographs are taken in a store or kiosk that sells skin care products.

Skin Care Product

Following the subject's visual analysis of the images, skin care product(s) can be suggested to the subject to address any perceived problems identified following such analysis. What is meant by a "skin care product" is a topical composition comprising cosmetically active agent. What is meant by a "cosmetically active agent" is a compound (e.g., a synthetic compound or a compound isolated from a natural source) that has a cosmetic or therapeutic effect on the skin, including, but not limiting to, anti-aging agents, lightening agents, darkening agents such as self-tanning agents, anti-acne agents, shine control agents, anti-microbial agents, anti-inflammatory agents, anti-mycotic agents, anti-parasite agents, sunscreens such as UVA/UVB blocking or absorbing agents, photoprotectors, antioxidants, keratolytic agents, detergents/surfactants, astringents, moisturizers, nutrients, amino acids, amino acid derivatives, minerals, plant extracts, animal-derived substances, vitamins, energy enhancers, anti-perspiration agents, astringents, deodorants, hair removers, hair growth stimulators, hair growth retarding agents, firming agents, anti-callous agents, and agents for nail and/or skin conditioning.

In one embodiment, the cosmetically-active agent is selected from, but not limited to, the group consisting of hydroxy acids, benzoyl peroxide, sulfur resorcinol, ascorbic acid, D-panthenol, hydroquinone, octyl methoxycinnimate, titanium dioxide, octyl salicylate, homosalate, avobenzone, polyphenolics, carotenoids, free radical scavengers, retinoids such as retinoic acid, retinol, and retinyl palmitate, ceramides, polyunsaturated fatty acids, essential fatty acids, enzymes, enzyme inhibitors, minerals, hormones such as estrogens, steroids such as hydrocortisone, 2-dimethylaminoethanol, copper salts such as copper chloride, peptides containing copper such as Cu:Gly-His-Lys, coenzyme Q10, lipoic acid, amino acids such a proline and tyrosine, vitamins, lactobionic acid, acetyl-coenzyme A, niacin, riboflavin, thiamin, ribose, electron transporters such as NADH and FADH2, and other botanical extracts such as aloe vera, witch hazel, and legumes such as soy beans, and derivatives and mixtures thereof. The cosmetically active agent will typically be present in the composition of the invention in an amount of from about 0.001% to about 20% by weight of the composition, e.g., about 0.01% to about 10% such as about 0.1% to about 5%.

Examples of vitamins include, but are not limited to, vitamin A, vitamin Bs such as vitamin B3, vitamin B5, and vitamin B12, vitamin C, vitamin K, and vitamin E and derivatives thereof.

Examples of hydroxy acids include, but are not limited to glycolic acid, lactic acid, malic acid, salicylic acid, citric acid, and tartaric acid.

Examples of antioxidants include but are not limited to, water-soluble antioxidants such as sulfhydryl compounds and their derivatives (e.g., sodium metabisulfite and N-acetyl-cysteine), lipoic acid and dihydrolipoic acid, resveratrol, lactoferrin, glutathione, and ascorbic acid and ascorbic acid derivatives (e.g., ascorbyl palmitate and ascorbyl polypeptide). Oil-soluble antioxidants suitable for use in the compositions of this invention include, but are not limited to, butylated hydroxytoluene, retinoids (e.g., retinol and retinyl palmitate), tocopherols (e.g., tocopherol acetate), tocotrienols, and ubiquinone. Natural extracts containing antioxidants suitable for use in the compositions of this invention, include, but not limited to, extracts containing flavonoids and isoflavonoids and their derivatives (e.g., genistein and diadzein), extracts containing resveratrol and the like. Examples of such natural extracts include grape seed, green tea, pine bark, and propolis.

Various other cosmetically-active agents may also be present in the skin care products. These include, but are not limited to, skin protectants, humectants, and emollients. The skin care products may also comprise chelating agents (e.g., EDTA), preservatives (e.g., parabens), pigments, dyes, opacifiers (e.g., titanium dioxide), and fragrances.

The following is an example of a manner of practicing a method of the present invention. Other manners may be practiced by those of ordinary skill in the art.

EXAMPLE

One embodiment of the present invention utilizes a kiosk that is intended to be an interactive tool from which subjects (e.g., potential customers) can evaluate their facial skin and decide upon a course of action to improve the appearance of the skin. The kiosk is designed such that a subject will have a series of images acquired of their face and the images will be presented to them one at a time along with questions relating to the displayed images.

In one example of the present invention, the kiosk comprises apparatus 100, as set forth in FIG. 1 (not to scale). Apparatus 100 is enclosed above and on three side (the side containing chin rest 6 in open for the subject to enter his/her head) with a frosted plastic glass (not shown). Apparatus 100, which is capable of taking four types of photographs of the subject, is set-up on table 15 having dimensions of 30" by 36". Half way along the long dimension of table 15 (about 18" from one end) and about 1 ⅝" in from the front end of table 15 there is chin rest 6 for the subject's chin. The height of chin rest 6 is about 12" above table 15. Across from chin rest 6 and exactly half way along the opposite end of the table 15 is camera 11 (Nikon D1X). Camera 11 is mounted so that the center of the camera lens of camera 11 is about 17" above the top of table 15. The distance between chin rest 6 and the front end of the lens of camera 11 is adjusted so that the subject's face substantially fills the camera frame of camera 11.

On the side of table 15 away from chin rest 6 are flash units 30a, 30b, 40a, 40b, 50a, and 50b (Broncolor Picolites, Sinar Bron, Allschwil, Switzerland) which are powered, respectively, by power packs 92, 92,93, 93, 91, and 91. The standard flash units 50a and 50b, which are used for taking a standard photograph, are mounted above camera 11 and angled down about 20 degrees. Flash units 50a and 50b are directed toward the center of the subject's face. Diffusing filters 51a and 51b (Broncolor Diffuser, Sinar Bran) are placed, respectively, in front of flash units 50a and 50b.

UVA flash units 30a and 30b, which are used for the ultraviolet A photography, are mounted on either side of camera 11 at about 14" from the edge of table 15 and at a height of about 20" from the top of table 15. UVA filters 31a and 31b (UG-11 filters, Schott Glass Technologies, Duryea, Pa. USA) are placed, respectively, in front of UVA flash units 30a and 30b. Blue flash units 40a and 40b, which are used for blue fluorescence photography, are also mounted on either side of the camera at about 14" from the edge of the table top and at a height of about 13" from the top of table 15. Blue filters 41a and 41b (Melles Griot, Irvine, Calif. USA) are placed, respectively, in front of blue flash units 40a and 40b. The UVA flash units 30a and 30b and the blue flash units 40a and 40b are directed to the center of the face of the subject.

The polarized flash units 20a and 20b (Broncolor Picolites), which are used for polarized light photography, are powered by power pack 90. Diffusing filters 21a and 21b (Broncolor Diffuser, Sinar Bron) are placed, respectively, in front of polarized flash units 20a and 20b, respectively. Linear polarizing filters 22a and 22b (Edmund Scientific, Barrington, N.J. USA) are placed, respectively, in front of diffusing filters 21a and 21b in a vertical orientation. Polarized flash unit 20a is positioned at about 4 ½" from the left edge and about 14" in from the proximal edge of table 15 and polarized flash unit 20b is positioned at about 4 ½" from the right edge and about 14" in from the proximal edge of table 15. The angle between either flash units 20a or 20b, the chin rest 6, and the camera 11 is about 45 degrees.

The method begins when the subject enters the kiosk image acquisition area and enters basic demographic information into a facial skin-care evaluation computer program (Microsoft Visual Basic, Microsoft Corporation, Redmond, Wash. USA) using a touch-screen monitor 70 (SecurePoint, SeePoint Technologies, Torrance, Calif.), which is mounted under table 15 and connected to the same computer running the computer program. The subject enters data into the computer program via monitor 70 (computer program runs MountFocus Runtime Keyboard and the keyboard present on monitor 70 was designed using MountFocus Keyboard designer programs (MountFocus Information Systems, Wilmington, Del. USA)), however, other input device such as a keyboard, a track ball, and a computer mouse may be used. Examples of such information include, but are not limited to, age and gender of the subject. Following the input of such demographic information, the computer program then instructs the subject to place their chin on chin rest 6 and indicates to the subject to close his/her eyes since apparatus 100 is ready to take photographs.

Upon touching monitor 70, the software makes a function call to an image acquisition and display software ("IDL software"; IDL, Research Systems, Inc., Boulder, Colo.) running on the same computer. The IDL software then triggers camera 11 to acquire a blue fluorescence photograph, a standard photograph, a polarized photograph, and an ultraviolet A photograph. The flash units 40a, 40b, 50a, 50b, 20a, 20b, 30a, and 30b are triggered sequentially through the use of a radio transceiver (Pocket Wizard Multimax, LPA Design, South Burlington, Vt. USA) using transceivers 95 (attached to power pack 90 and operating in receiver mode), 96 (attached to power pack 91 and operating in receiver mode), 97 (attached to power pack 92 and operating in receiver mode), 98 (attached to power pack 93 and operating in receiver mode), and 99 (attached to the hot shoe of camera 11 and operating in transmitter mode). A Topas A2 power pack (Sinar Bron) is used for power packs 90 and 91 and a Primo 4 power pack (Sinar Bron) is used for power packs 92 and 93. The radio transceiver causes the activation of the pairs of flash units in response to the shutter release of camera 11.

Prior to taking the blue fluorescence photograph, the IDL software makes a call to servo motor 80, using a Mini SSC II circuit board (Scott Edwards Electronics, Sierra Vista, Ariz. USA), to move long pass filter 81 (Kodak Wratten No. 8, Eastman Kodak, Rochester, N.Y. USA) in front of the lens of camera 11. After this movement, the blue fluorescence photograph is taken. Following the taking of this photograph, the IDL software then makes another call to servo motor 80 to move long pass filter 81 away from the lens of camera 11. The IDL software then instructs the camera to take the remaining three images. Apparatus 100 is able to acquire these four images in about 10 seconds.

At this point, the four images just acquired are stored in the memory of camera 11 as separate data files. The IDL software then makes function calls to these data files and requests these files be transferred to the computer running the computer software and saved to its hard disk with a file name that indicates the apparatus used, subject identifier, and the type of image.

The subject is then presented on monitor 70 with a registration form. Examples of such questions include e-mail address, places where they buy skin-care products, ethnic background, and amount and type of skin-care products that they have purchased in the past (e.g., the past year).

The subject then begins reviewing each of the four images on monitor 70 and answers questions, presented on monitor 70, about each image. The computer program calls the IDL software and requests that a particular saved image be loaded from the hard disk and resized to fit in the screen display area. Once the image is displayed, the IDL software then returns control to the computer program. The facial image display area is roughly half of monitor 70. The other half of the screen of monitor 70 displays a series of questions relating to the particular displayed image. To assist the subject in the review of his/her images, the computer program may also display on monitor 70 images of other people as comparisons.

As the subject advances to the next page, the computer program calls IDL program and requests that a particular saved image be loaded from the hard disk and resized to fit in the screen of monitor 70 area as discussed above. This procedure continues until all four images have been displayed and all questions have been answered by the subject.

Upon viewing the standard photograph, the subject is then presented with questions regarding the surface of his/her skin. Examples of such questions include, but are not limited to, whether they have any fine lines, wrinkles, loss of elasticity or firmness, large visible pores, sensitive skin, and rough or smooth skin, as well as the severity and location of such conditions. Other questions include, but are not limited to, the frequency and severity of irritation from skin care products.

Upon viewing the polarized photograph, the subject is asked questions regarding the oiliness of their skin. Examples of such questions include, but are not limited to, whether they have normal, dry, oily, or selective oily skin (e.g., oil in certain areas such as above the eyebrows and on the tip of the nose).

Upon viewing the ultraviolet A photograph, the subject is asked questions regarding the visualization of pigmentation of the face (e.g., brown spots). Examples of such questions include, but are not limited to, the amount and location of such pigmented spots.

Upon viewing the blue fluorescence photograph, the subject is asked questions regarding acne. Examples of such questions include, but are not limited to, the severity and frequency of his/her breakouts.

As described above, the images from camera 11 are displayed on the computer monitor 70. However, because the number of available screen pixels are less than the number of actual image pixels taken by the digital photograph, only a small percentage of the original image can actually be displayed if the image is to be shown on the screen in its entirety while maintaining aspect ratio. For the case of the Nikon D1X, which stores 6 million pixels per image, display of the digital image in a portrait orientation on a computer screen having a resolution of 1024×768 results in display of only 1 out of every 18 pixels. In such a down-sampled image presentation, fine detail of the skin taken by camera 11 is not fully displayed.

The solution to this problem is to use a technique whereby a 256×256 box (display kernel) appears directly over the area of interest and shows all the image pixels actually acquired by camera 11 for such area. The effect is an in-place magnification of a small area of the image on monitor 70. The apparent magnification, shown as this display kernel, can be passed over various areas of the image selected by the subject. Thus, this is an example of 1:1 image display (where every image pixel is shown on the screen within a small display kernel). True magnification of the image can also be accomplished by interpolating the data between pixels and creating additional pixels, thereby providing magnification of select areas of the image. The subject selects the magnification of such area by touching the area of interest displayed on the monitor 70.

Following the input of the answers from the subject, the computer program then proceeds to suggest skin care products for the subject. Each question in the computer program is associated with a skin condition. For example, the question "How often does your skin breakout?" is associated with acne. As the subject answers each question, the corresponding skin condition is assigned a degree. For example, the acne question has four degrees corresponding to the four answer choices: Always, Weekly, Monthly and Never. After the subject answers all the questions, the skin conditions questioned by the computer program are ranked according to severity. This ranking is accomplished by passing all of the degree values entered by the subject to a relational database stored procedure contained within a relational database (Microsoft SQL, Microsoft Corporation, Redmond, Wash. USA) that is on the same computer.

A database table contained with the relational database contains a record for each skin problem type and degree. A "degree weight" is assigned to each record, which facilitates the ranking of the skin conditions. For example, if the subject answers "Always" for the above acne question, and "Yes" to the question "Do you notice any loss of firmness on your face?" the acne skin condition may have a higher rank than the loss of firmness condition. However, if the subject answers "Weekly" to the above acne question and "Yes" to the loss of firmness question, the loss of firmness condition may be ranked higher.

After the skin conditions are ranked, the top three conditions, along with the subject's skin type, e.g., normal, dry, or oily, are passed to another relational database stored procedure contained within the relational database. Using these values, this procedure queries a second database table that contains all of the possible combinations of skin conditions along with skin type. Each such record in the table contains a list of recommended products based on these values. This corresponding list of recommended products for that subject's condition is then passed back to the computer program.

Finally, the computer program creates a printout using Crystal Reports (Seagate Corporation, Scotts Valley, Calif. USA) for the subject including the suggested skin care products and pictures of the subject with information about the various skin conditions. At the conclusion of computer program, the subject will indicate whether or not the images should be kept or deleted.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of photographing the skin of a person, said method comprising the steps of:

i) illuminating said skin with at least one light source, where the light emitted from said light source is filtered using a polarizing filter; and ii) capturing the image of said illuminated skin with a camera wherein the angle formed by said light source, said skin, and said camera is from about 35 degrees to about 55 degrees, and wherein said light filtered using said polarizing filter is not filtered with another polarizing filter prior to such light entering said camera.

2. A method of claim 1, wherein said polarizing filter is a linear polarizing filter.

3. A method of claim 1, wherein said angle formed by said light source, said skin, and said camera is about 45 degrees.

4. A method of claim 2, wherein said linear polarizing filter is arranged such that the electric field of the emitted light is about perpendicular to the plane formed by said light source, said person's skin, and said camera.

5. A method of claim 2, wherein said angle formed by said light source, said skin, and said camera is about 45 degrees.

6. A method of claim 4, wherein said linear polarizing filter is arranged such that the electric field of the emitted light is about vertical and the plane formed by said light source, said person's skin, and said camera is about horizontal.

7. A method of claim 4, wherein said angle formed by said light source, said skin and said camera is about 45 degrees.

8. A method of claim 6, wherein said angle formed by said light source, said skin, and said camera is about 45 degrees.

9. A method of promoting a skin care product, said method comprising:
   (i) illuminating the skin of a person with at least one light source, where the light emitted from said light source is filtered using a polarizing filter;
   (ii) capturing the image of such illuminated skin with a camera, wherein the angle formed by said light source, said skin, and said camera is from about 35 degrees to about 55 degrees;
   (iii) presenting said image to said person; and
   (iv) suggesting skin care products based upon said person's review of said image; wherein said light filtered using said polarizing filter is not filtered with another polarizing filter prior to such light entering said camera.

10. A method of claim 9, wherein said method further comprises presenting said person with one or more questions relating to said presented image and said suggestion of skin care products is based upon said person's answers to said one or more questions.

11. A method of claim 9, wherein said polarizing filter is a linear polarizing filter.

12. A method of claim 9, wherein said angle formed by said light source, said skin, and said camera is from about 45 degrees.

13. A method of claim 10, wherein said polarizing filter is a linear polarizing filter.

14. A method of claim 10, wherein said angle formed by said light source, said skin, and said camera is about 45 degrees.

15. A method of claim 11, wherein said linear polarizing filter is arranged such that the electric field of the emitted light is about perpendicular to the plane formed by said light source, said person's skin, and said camera.

16. A method of claim 11, wherein said angle formed by said light source, said skin and said camera is about 45 degrees.

17. A method of claim 13, wherein said linear polarizing filter is arranged such that the electric field of the emitted light is about perpendicular to the plane formed by said light source, said person's skin, and said camera.

18. A method of claim 13, wherein said angle formed by said light source, said skin and said camera is about 45 degrees.

19. A method of claim 15, wherein said linear polarizing filter is arranged such that the electric field of the emitted light is about vertical and the plane formed by said light source, said person's skin, and said camera is about horizontal.

20. A method of claim 15, wherein said angle formed by said light source, said skin and said camera is about 45 degrees.

21. A method of claim 17, wherein said linear polarizing filter is arranged such that the electric field of the emitted light is about vertical and the plane formed by said light source, said person's skin, and said camera is about horizontal.

22. A method of claim 17, wherein said angle formed by said light source, said skin, and said camera is about 45 degrees.

23. A method of claim 19, wherein said angle formed by said light source, said skin, and said camera is about 45 degrees.

24. A method of claim 21, wherein said angle formed by said light source, said skin, and said camera is about 45 degrees.

* * * * *